(12) United States Patent
Kraus

(10) Patent No.: US 7,174,982 B2
(45) Date of Patent: Feb. 13, 2007

(54) DISPLACEABLE SUPPORT STAND

(75) Inventor: Martin Kraus, Hüttlingen (DE)

(73) Assignee: Carl-Zeiss-Stiftung trading as Carl Zeiss (DE)

( * ) Notice: Subject to any disclaimer, the term of this patent is extended or adjusted under 35 U.S.C. 154(b) by 0 days.

(21) Appl. No.: 10/855,220

(22) Filed: May 27, 2004

(65) Prior Publication Data
US 2004/0262866 A1 Dec. 30, 2004

(30) Foreign Application Priority Data
Jun. 27, 2003 (DE) ................ 103 29 985

(51) Int. Cl.
*B60V 1/04* (2006.01)
(52) U.S. Cl. .................. 180/125; 180/117; 180/164
(58) Field of Classification Search ............... 180/116, 180/127, 125, 117, 164, 209; 280/43, 43.14, 280/43.17, 43.23, 43.24
See application file for complete search history.

(56) References Cited

U.S. PATENT DOCUMENTS

| | | | | |
|---|---|---|---|---|
| 2,671,242 A | * | 3/1954 | Lewis | 16/33 |
| 2,938,590 A | * | 5/1960 | Barnett | 180/125 |
| 2,967,458 A | * | 1/1961 | Stone, Jr. | 359/375 |
| 3,052,483 A | * | 9/1962 | Petersen | 180/123 |
| 3,177,959 A | * | 4/1965 | Gaska | 180/120 |
| 3,237,708 A | * | 3/1966 | Strasser et al. | 180/121 |
| 3,613,821 A | * | 10/1971 | Kerr et al. | 180/125 |
| 3,810,522 A | * | 5/1974 | Morgan et al. | 180/116 |
| 3,899,187 A | * | 8/1975 | Millett | 280/43.24 |
| 3,942,865 A | * | 3/1976 | Rand | 359/430 |
| 4,573,396 A | * | 3/1986 | Streetman et al. | 89/36.08 |
| 4,815,926 A | * | 3/1989 | Chaffee et al. | 414/676 |
| 5,609,316 A | * | 3/1997 | Tigliev | 248/123.11 |

FOREIGN PATENT DOCUMENTS

| | | |
|---|---|---|
| DE | 37 28 527 A1 | 3/1988 |
| DE | 199 52 477 A1 | 5/2001 |
| WO | WO 98/53244 | 11/1998 |

* cited by examiner

*Primary Examiner*—Anne Marie Boehler
(74) *Attorney, Agent, or Firm*—Gerald E. Hespos; Anthony J. Casella

(57) ABSTRACT

A displaceable support stand (1) includes a support stand base (5) with a support surface (6) which is adapted to rest on the ground, a lifting device for lifting the support stand base (5) and therewith the support stand (1) above the ground and a displacement device which permits displacement of the support stand (1). The lifting and the displacement devices can be embodied by a device for producing an air cushion. A device of that kind can include for example a compressor (18), an accumulator (20) for the power supply for the compressor (18) and air nozzles (16).

19 Claims, 4 Drawing Sheets

DISPLACEABLE SUPPORT STAND

BACKGROUND OF THE INVENTION

1. Field of the Invention

The present invention concerns a displaceable support stand and in particular a displaceable support stand for optical viewing devices, for example surgical microscopes.

2. Description of the Related Art

A typical support stand as is used in particular for surgical microscopes is displaced by means of caster wheels, as are also known for example from hospital beds. When the support stand has reached its final position, further movement is prevented by actuation of a locking brake. Usually the locking brake acts directly on the caster wheels or, in the form of lowerable feet, directly on the floor on which the support stand is supported. A support stand of that kind is described for example in WO 98/53244. The support stand described therein includes a support stand base which has caster wheels and lowerable support feet. The support feet are lowered in the working position of the support stand while, for displacement of the support stand, they can be raised, in which case the caster wheels bear against the ground. Support stands of that kind however are relatively difficult to manoeuvre within tight spaces, in particular if relatively high forces have to be applied by the operating personnel in the manoeuvring procedure, because the support stand is of great weight. Fine positioning of the support stand can therefore be difficult.

In order to improve the mobility of a support stand, DE 199 52 447 A1 proposes that, in addition to wheels for straight-ahead travel and pivotable steering wheels on the support stand, the stand also has extendable additional wheels, by means of which, if required, it is possible to provide for mobility of the support stand transversely with respect to the direction of rolling movement of the straight-ahead wheels.

In the case of the above-described support stands, it is possible for the support stand to travel over cables when it is being displaced. In that case there is the danger of the cables being damaged or squashed by the wheels, or displaced in an undesirable fashion. A similar risk involves the wheels running over feet of the operating personnel, which can result in injury.

In addition, in the support stands in the state of the art, the locking brake which is intended to prevented unwanted displacement of the support stand requires a relatively high level of mechanical complication and expenditure and possibly high operating forces.

Therefore the object of the present invention is to provide a displaceable support stand which is improved in comparison with the state of the art.

SUMMARY OF THE INVENTION

A displaceable support stand according to the invention includes a support stand base with a support surface adapted for resting on the ground, a lifting device for lifting the support stand base and therewith the support stand above the ground and a displacement device which permits displacement of the support stand. In that respect, the term displacement device is intended to mean any rolling, sliding or other device which permits displacement of the support stand. In that respect it is immaterial whether the displacement is effected manually or motor-driven.

The support surface permits the support stand to rest on the ground in a stable condition. In that case, by virtue of its inherent weight and the friction resulting therefrom between the support surface and the ground, the support stand is secured to prevent unintended displacement thereof. Therefore the support surface acts together with the inherent weight of the support stand as an almost immovable brake, particularly if the inherent weight of the support stand is high. The support stand according to the invention therefore does not require locking brakes which are structurally complicated and/or complicated in terms of the forces involved, for the displacement device.

For displacement of the support stand according to the invention, the support stand base is lifted by means of the lifting device so that its support surface is no longer in contact with the ground. Displacement of the support stand can then be effected by means of the displacement device manually or by way of a drive means. As soon as the support stand has reached the desired position the support stand base and therewith the support surface are lowered on to the ground again and thus the support stand is restored to its stable condition of standing on the ground.

Often, the floors on which the support stand is to rest are flat, as is the case for example in operating theatres. Advantageously therefore the support surface is of such a configuration that it can rest flat on the floor. When a flat floor surface is involved, the fact that the support surface rests flat thereon permits good contact between the support surface and the floor, whereby it is possible to afford a particularly good brake effect.

The lifting device of the displaceable support stand according to the invention can be operated by compressed air. Pneumatically raising and lowering the support stand is a structure which is inexpensive in comparison with an electromechanical lifting and lowering arrangement.

In particular the support stand may include one or more compressed air nozzles for producing an air cushion under the support surface. The compressed air nozzles can then serve both as a lifting device and also as a displacement device. In that configuration of the support stand, for displacement thereof the air cushion is activated by means of the compressed air nozzles in order to lift the support stand. Upon displacement of the support stand the air cushion then replaces the wheels or casters which are usual in the state of the art. Even relatively high loads can be very easily and precisely moved in any directions on the air cushion. When an air cushion is involved, constraint guidance effects as occur when using wheels or rollers by virtue of the rolling direction thereof are completely eliminated. In addition, relatively small irregularities in the floor surface such as for example joins which can represent an obstacle to wheels or rollers can be bridged over by means of the air cushion. By boosting the air cushion, it can be adapted to the size of the irregularities in the floor surface.

For the purposes of securing the support stand in position, the air cushion is retracted in such a way that the support stand rests gently on the ground. Then, as stated above, the weight of the support stand together with the support surface acts as a brake for the support stand.

If the lift height of the air cushion is small, then the risk of injury to the feet of operating personnel is also slight as the support stand cannot pass over a foot. That is the case in particular if the lift height of the air cushion is not more than 20 mm and in particular is not more than 12 mm.

In order to stabilise the air pressure of the air cushion, a flexible skirt can be provided around the support stand base. The skirt serves at the same time to push aside or fend off cables or other objects. In particular that also makes it possible to reduce the risk of injury to the operating personnel, even with an air cushion lift height which is greater than about 12–20 mm.

The support stand according to the invention can be provided with a hose-connected compressed air supply. That means that the radius of movement of the support stand is admittedly limited to regions in which a compressed air supply is available, but as a counterpart thereto the support stand does not need to be equipped to produce compressed air. As an alternative or in addition to the hose-connected compressed air supply however the support stand can also be provided with a compressed air storage means, which enhances its freedom of movement. If the support stand has the compressed air supply by way of a compressed air storage means as a supplement to the hose-connected compressed air supply, it can serve for example to bridge over sections in which a hose-connected compressed air supply is not possible, when the support stand is being displaced.

In an alternative configuration the displaceable support stand includes a compressor which can be supplied with power by way of a cable arrangement or by an accumulator or battery. The fact of producing the compressed air on or in the support stand itself means that it is possible to eliminate connection of the support stand to compressed air conduits. In that respect in particular the mobility of the support stand is enhanced as it can be used even where no compressed air conduit is available within the range of the support stand. The support stand can be used in particular in an independent fashion if the power supply is by way of an accumulator or a battery as then there is also no need for an electrical connection in range of the support stand. In particular in that way the support stand can be moved over relatively great distances. In addition for example in OP operation of a support stand for an surgical microscope the accumulator or battery system can also be used as a safety system or back-up power system in the event of power failures. In the parked condition or in a stationary mode of operation, the support stand or the accumulator can be connected to the power supply mains, in which case the accumulator can be automatically charged. If the support stand is displaced in that condition, the power for that purpose can be taken either from the power supply mains or from the accumulator.

As further advantages, the compressor and/or the accumulator or battery of the support stand increase the overall weight thereof and thus enhance its stability and steadiness in the lowered condition. In addition the compressor, the accumulator or the battery can serve as a counterweight for the support stand arms.

In the displaceable support stand according to the invention the compressed air, besides being used for forming the air cushion, can also be used for actuating compressed air-operated drives and/or brakes.

As an alternative or in addition to one or more compressed air nozzles, the displaceable support stand according to the invention can be provided with extendable and optionally height-adjustable wheels or rollers. If the support stand does not have any compressed air nozzle, the extendable wheels or rollers represent both the lifting device and also the displacement device of the support stand. Otherwise the extendable wheels or rollers serve to bridge over regions which are unsuitable for continuing movement of the support stand by means of the air cushion, either because there are major floor unevenness configurations such as for example thresholds which cannot be compensated by means of the air cushion, or because the support stand has to travel over gaps, for example in the case of an elevator.

Extension of the extendable wheels or rollers can be effected mechanically, for example by way of a lever mechanism, or electrically, in which respect the power supply for electrical extension purposes can be embodied by way of the power supply mains or an accumulator.

In a particular configuration of the support stand according to the invention the rollers are of such a nature that, when the support stand base is raised, the rollers rest loosely on the ground and, in the event of an abrupt failure of the compressed air, are clamped, that is to say they carry the support stand. In that way, in the event of the air cushion abruptly collapsing, it is possible to ensure that the support surface is not set down on the floor with a jerk. More specifically, the fact of the support stand being set down with a jerk can damage it or can result in a jerky braking effect such as to damage the support stand.

As the wheels or rollers in conjunction with an air cushion only serve for bridging over unevenness in a surface and/or as a safety system, only relatively low demands in terms of design and fine manoeuvrability need to be made thereon.

Optionally the support surface of the support stand according to the invention can be of a flexible and/or vibration-damping configuration. With that design configuration, it is possible to compensate for unevenness of the floor and any vibrations which are possibly present such as for example vibrations in a building. Such a configuration can be advantageous in particular if for example besides an item of equipment which is to be supported in a low-vibration manner such as for example a microscope, vibration-generating analysis or manipulation devices are also fitted to the support stand.

The support stand according to the invention can be designed as a support stand for optical viewing devices such as for example microscopes and in particular as a support stand for surgical microscopes.

Further features, properties and advantages of the support stand according to the invention will be apparent from the description hereinafter of embodiments by way of example with reference to the accompanying drawings.

DETAILED DESCRIPTION OF THE PREFERRED EMBODIMENTS

Figure 1:
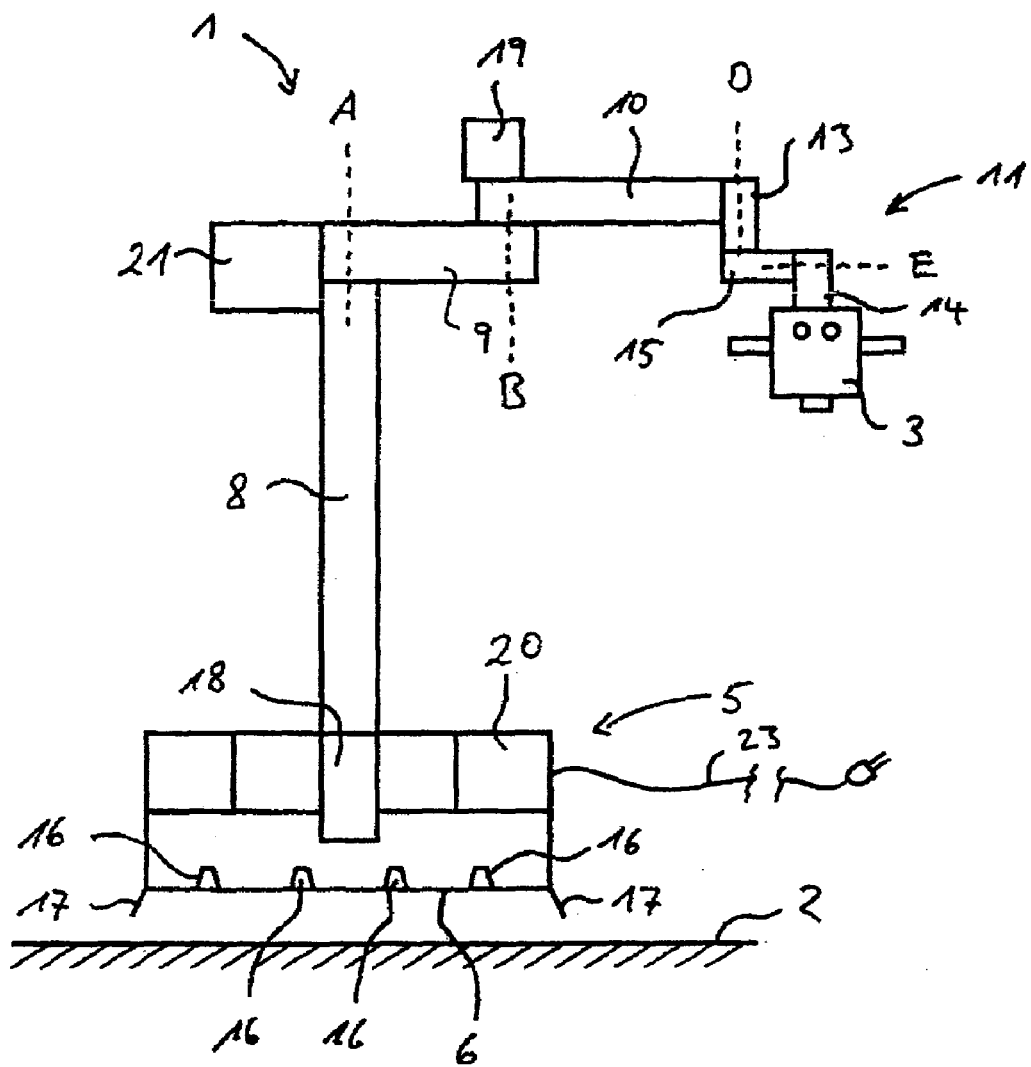
FIG. 1 diagrammatically shows a first embodiment of the support stand according to the invention.

A support stand 1 according to the invention with a microscope 3 secured thereto, which in the illustrated embodiment is an surgical microscope, is diagrammatically shown in FIG. 1. The support stand base 5 of the support stand 1 is shown in section.

The support stand 1, as support stand components, includes a height-adjustable support stand column 8, a carrier arm 9, a spring arm 10 and a microscope suspension assembly 11 which in turn includes a connecting element 13, a pivot arm 15 and a holding arm 14. At its one end the carrier arm 9 is connected to the support stand column 8 rotatably about an axis A. An end of the spring arm 10 is mounted to the other end of the carrier arm 9 rotatably about an axis B which is parallel to the axis A so that the carrier arm 9 and the spring arm 10 form a hinge arm. The other end of the spring arm 10 is formed by a tilting mechanism (not shown) to which the microscope suspension assembly 11 is fixed and which permits a tilting movement of the microscope suspension assembly 11.

The microscope suspension assembly 11 has an axis of rotation D, a pivot axis E and a tilt axis (not shown) about which the microscope can be rotated, pivoted and tilted respectively. The microscope suspension assembly 11 is fixed to the outer end of the spring arm 10 rotatably about the axis of rotation D, with a connecting element 13. The axis of rotation D extends along the connecting element 13. Adjoining the connecting element 13 is a pivot arm 15, by means of which the microscope 3, more precisely a holding arm 14 which is mounted to the pivot arm 15 and to which the microscope 3 is fixed by means of a microscope holder (not shown) can be pivoted about the pivot axis E. The pivot axis E extends through the pivot arm 15. The angle between the pivot arm 15 and the connecting element 13, that is to say the angle between the pivot axis E and the axis of rotation D, can be varied by means of an adjustment mechanism disposed between the connecting portion 13 and the pivot arm 15.

The tilt axis which permits a tilting movement of the surgical microscope 3 extends through the holding arm 14, perpendicularly to the plane of the drawing. The surgical microscope 3 is secured to the holding arm 14 by means of a microscope holder (not shown).

The column 8 of the support stand 1 rests on a support stand base 5 to which it is fixedly connected and the underside of which forms a contact support surface 6 for resting on the ground 2. Arranged in the support surface 6 are air nozzles 16 by way of which compressed air can issue if required so that an air cushion is formed between the support surface 6 and the floor 2 and lifts the support stand base 5 (and therewith the support stand 1 generally). Provided at the outer edge of the support surface 6 is a skirt 17 which serves primarily for stabilising the air pressure in the air cushion built up by means of the air nozzles 16 under the support surface 6, but which is also intended to prevent the support stand from running over objects when the support stand 1 is raised.

Figure 1A:
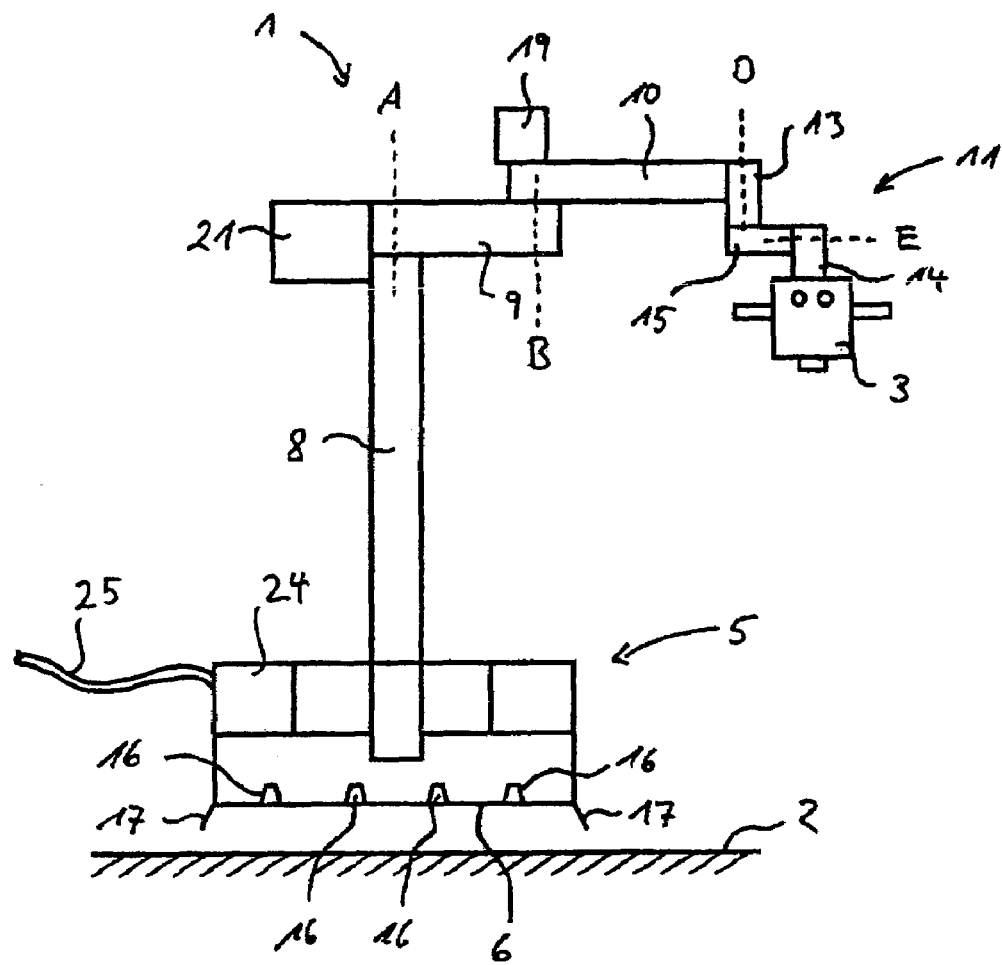
FIG. 1a shows a variation of this first embodiment.

The compressed air for building up the air cushion is made available by a compressed air supply which in the present embodiment includes a compressor 18 as a compressed air generator and at least one accumulator 20 arranged in the support stand base 5 for supplying the compressor 18 with electrical power. In addition the accumulator 20 can also serve as an emergency power unit for items of equipment fixed to the support stand 1, such as for example the microscope 3 itself, a light source 19 or an operating element 21. The accumulator 20 can be connected to an external power supply by means of a cable 23 for charging purposes. During the charging operation the compressor 18 is supplied with electrical power by way of the external power supply. Instead of a compressor 18 and an accumulator 20 the compressed air supply can also include a compressed air reservoir 24 which is or can be connected to the nozzles and which can be connected to an external compressed air supply by means of compressed air hoses 25 for the filling procedure as shown in FIG. 1a. The compressor 18 and the accumulator or accumulators 20 however additionally afford the advantage that they form a counterweight to the carrier arm 9 and the spring arm 10 and thus increase the stability and sturdiness of the support stand. It will be appreciated that, in alternative configurations of the support stand, the power or compressed air supply may also be effected completely by a cable arrangement and a hose arrangement respectively.

The air nozzles 16 together with the compressed air supply form a lifting device, by means of which the support stand 1 can be lifted when required.

As the air cushion does not oppose any resistance worth mentioning to movement of the support stand 1 parallel to the floor, the support stand 1 can be easily displaced when the air cushion has been built up. In contrast to rollers the air cushion also does not have any preferential direction of movement so that the support stand 1 can be moved in any desired direction without a large amount of force being applied. The air cushion therefore affords the operating personnel particularly good manoeuvrability of the support stand 1. The air nozzles 16 together with the compressed air source therefore not only form the lifting device of the support stand 1 but also a displacement device which permits displacement of the support stand 1.

When the support stand 1 has reached the desired position the compressed air supply to the air nozzles 16 is interrupted so that the air cushion under the support surface 6 is shut down and the support surface 6 comes to rest on the floor 2. As soon as that has happened, displacement of the support stand 1 is possible, if at all, only by applying a very great deal of force. There is therefore no need for brakes which are intended to prevent unintentional displacement of the support stand 1. In that respect, the air cushion should be shut down in such a way that the support stand 1 is set down gently on the floor 2. That can be achieved for example by suitable control of the feed of compressed air to the air nozzles 16 when shutting down the air cushion.

The lift height of the support stand 1 is 12 mm but it can also be greater or smaller, depending on the respective needs involved. For varying the lift height, the support stand 1 may include for example an adjusting mechanism for setting the air pressure in the air cushion. The smaller the lift height of the support stand is, the correspondingly more sensitive is the reaction of the support stand 1 to unevenness and irregularities in the floor, when the support stand is moving. On the other hand, with an increasing lift height, there is an increased danger of running over cables or the like and squashing them when the support stand is lowered. The same applies for example to the feet of the operating personnel so that a lift height which is not excessive is appropriate, in the sense of reducing the risk of injury. The skirt 17 can also obviate the risk of injury as for example it encounters a foot before passing over it and thus performs a warning function for the person in question.

In the illustrated embodiment the support surface 6 is of a flexible and vibration-damping configuration so that on the one hand it is possible to compensate for any irregularities and unevenness in the floor which may be present, when the support surface 6 is resting on the floor, while on the other hand it is possible to suppress the transmission of building vibration to the microscope 3 by way of the support stand 1.

Figure 2:
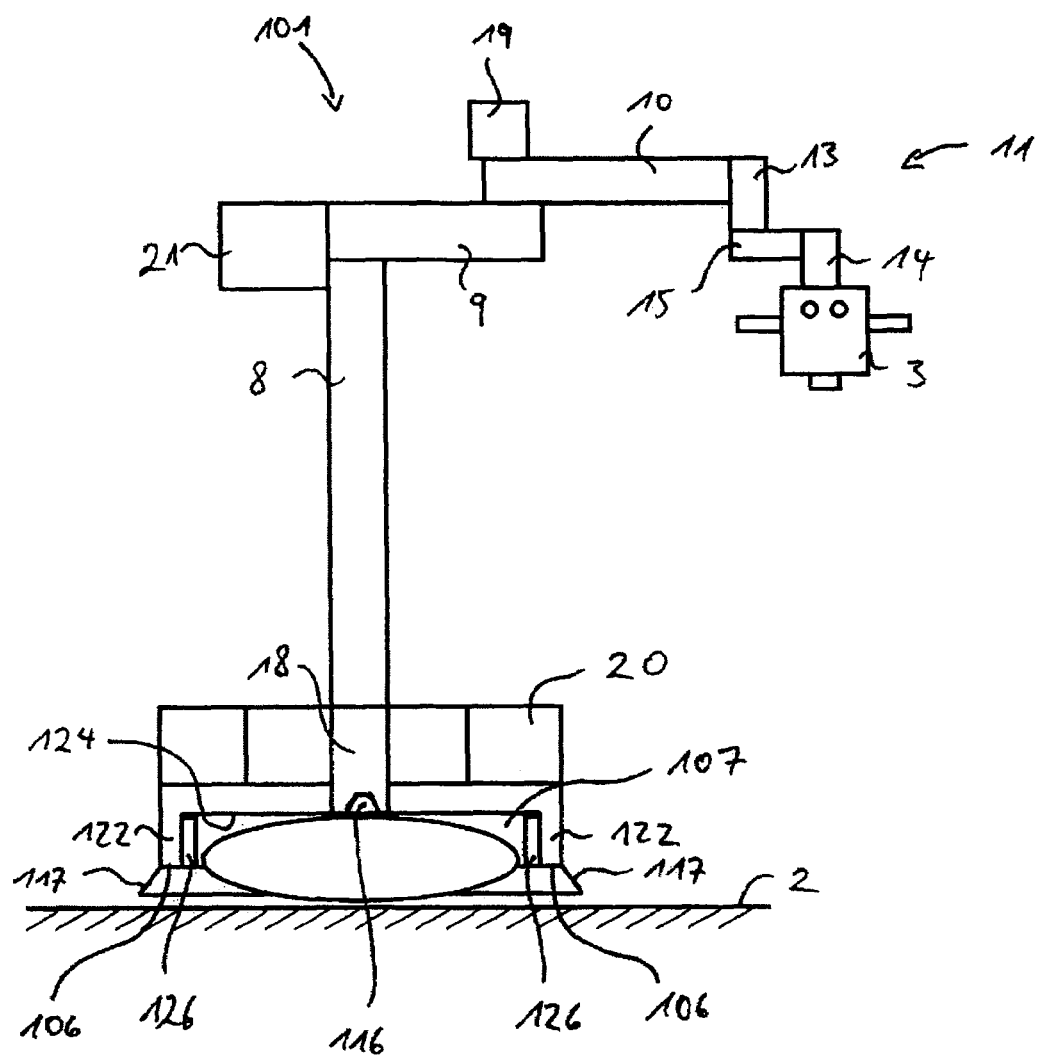
FIG. 2 diagrammatically shows a second embodiment of the support stand according to the invention.

A second embodiment of the support stand according to the invention is diagrammatically shown in FIG. 2. In this case the support stand base is once again shown in section. The support stand 101 of the second embodiment differs from the support stand 1 of the first embodiment only in regard to the configuration of the support stand base 105. Therefore, the other components of the support stand 101 will not be further discussed hereinafter.

In the second embodiment the support stand base 105 includes a cavity which is open towards the floor and which is laterally delimited by a peripheral wall 122 and which forms a buoyancy or upthrust chamber 107 in which the air cushion is formed. For the purposes of building up the air cushion, disposed in the chamber wall which is opposite to the opening of the chamber, or in the chamber top 124, are one or more air nozzles 116 which, like the air nozzles 16 in the first embodiment, can be supplied with compressed air by way of an internal or external compressed air supply when the support stand 101 is to be raised or displaced. The configuration of the compressed air supply corresponds to that of the first embodiment and is therefore not further described at this juncture.

In the present embodiment the underside of the peripheral wall 122 surrounding the upthrust chamber 107 forms the support surface 106. A flexible skirt 117 arranged at the outside of the peripheral wall 122 serves for stabilising the air pressure in the air cushion.

Arranged in the interior of the upthrust chamber 107 are rollers or wheels 126 (hereinafter, for the sake of simplicity, mention will only be made of rollers, without the use of wheels being excluded thereby), which if required can be extended so that they project beyond the support surface 106. The rollers 126 serve inter alia to perform the function of a displacement device if no compressed air is available. In addition the rollers 126 can come into use if for example the support stand is to travel across an elevator gap or the like.

The rollers 126 can also be designed in such a way that they project a little towards the floor, beyond the support surface 106. That arrangement provides that, in the event of an abrupt drop in pressure, the support stand 101 does not come to a stop with a jerk, which helps to avoid damage to the support stand and/or the microscope secured thereto. In addition, it is possible to prevent the support surface 106 being set down hard on the ground in the event of a sudden failure of pressure, if the rollers 126 have a springing arrangement. Then, when the support stand is set down, the rollers 116 are gradually pressed into the support stand base 105 against the spring force of the springing arrangement so that the support surface comes to rest on the floor.

Figure 3:
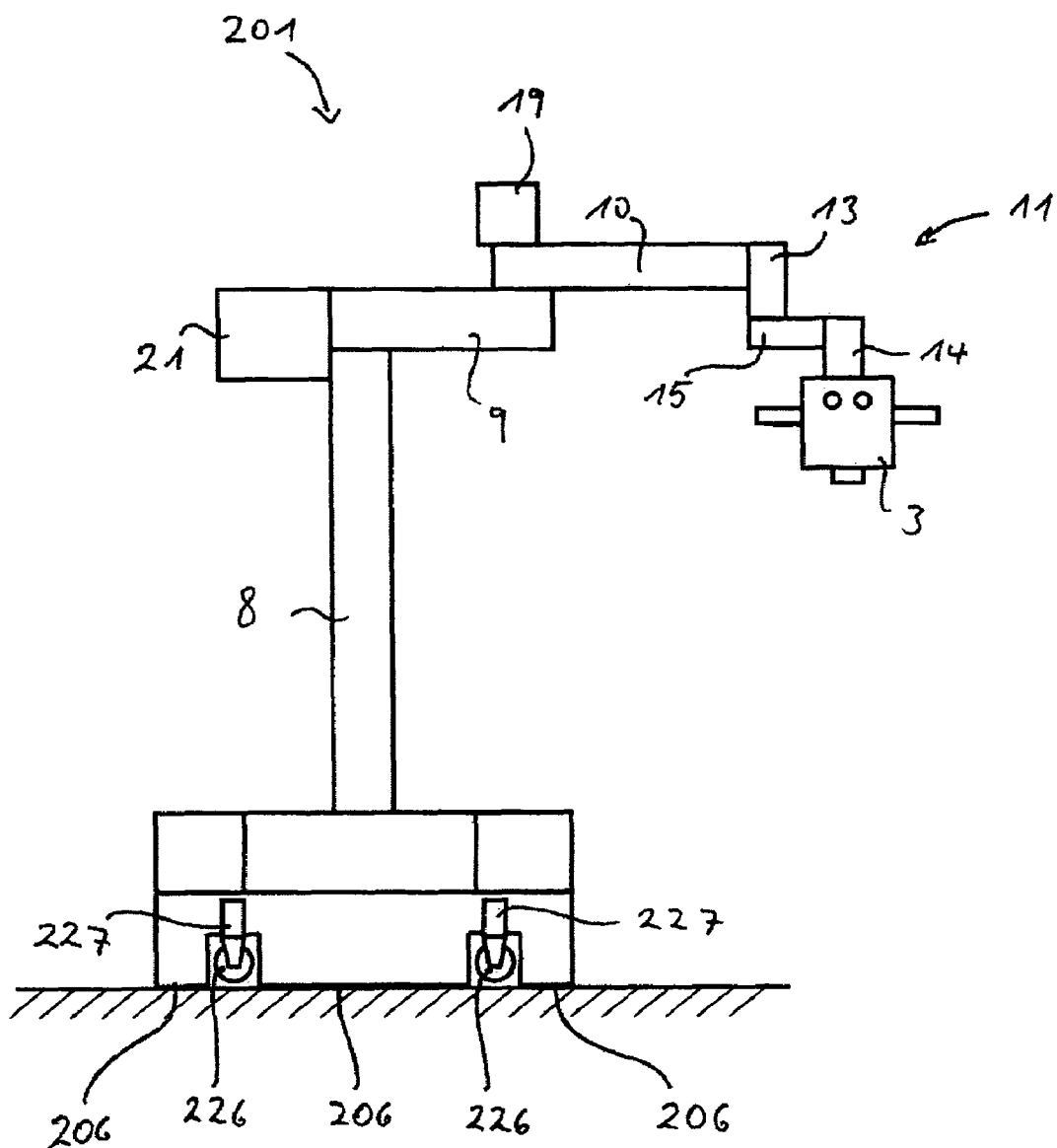
FIG. 3 diagrammatically shows a third embodiment of the support stand according to the invention.

Besides the function of the displacement unit and the protective function for protecting the support stand however the rollers can also perform the function of a part of the lifting device. A corresponding support stand 201 is diagrammatically shown in FIG. 3 as a third embodiment. Components which are the same as those of the support stand 101 in the second embodiment are denoted by the same references in both embodiments. Rollers as are known from the state of the art for use with support stands can be used as the rollers 226. They are arranged in or on the support stand 205 in such a way that they can be retracted into and extended from the support surface 206. A hydraulic, pneumatic, electrical or mechanical roller lifting device 227 can be used for extending and retracting the rollers 226. The support stand 201 of the third embodiment does not have a device for producing an air cushion.

For displacement of the support stand 201 the rollers 226 are lowered by means of the roller lifting device 227, whereby the support stand 201 is lifted and can be displaced by means of the rollers 226. When the support stand 201 has reached its target position, the rollers 226 are retracted by means of the roller lifting device 227 again so that the support surface 206 is set down on the floor and, together with the weight of the support stand, operates as a brake. Displacement of the support stand 201 is then possible, if at all, only by applying a large amount of force. In contrast to displaceable support stands according to the state of the art, there is no need for expensive and complicated mechanical direct braking of the rollers 226.

In all embodiments in which the support stand has its own compressed air supply or is supplied with compressed air by way of a hose arrangement, the movement of the support stand members 8, 9, 10 and/or the microscope suspension arrangement 11 about the axes A–F can be effected by means of compressed air-operated actuators. Likewise the brakes for braking the support stand members 8, 9, 10 or the microscope suspension arrangement 11 can be compressed air-actuated.

What is claimed is:

1. An optical observation system comprising:
   a microscope and
   a displaceable microscope support stand carrying the microscope, the displaceable support stand comprising a support stand base which includes a support surface adapted for resting on the ground, a compressed air-operated lifting device for lifting the support surface above the ground, the lifting device including at least one compressed air nozzle for producing an air cushion under the support surface, a displacement device which permits displacement of the support stand, and wheels or rollers which are extendable such as to project beyond the support surface.

2. The optical observation system of claim 1, wherein the support surface is an underside of the support stand base which is adapted for resting flat on the ground.

3. The optical observation system of claim 1, wherein there is a flexible skirt around the support surface.

4. The optical observation system of claim 1, comprising a compressor for producing the compressed air.

5. The optical observation system of claim 4, having a cable-connected power supply for the compressor.

6. The optical observation system of claim 4, having an accumulator or a battery as the power supply for the compressor.

7. The optical observation system of claim 1, having a hose-connected compressed air supply.

8. The optical observation system of claim 1, having a compressed air storage means.

9. The optical observation system of claim 1, wherein the rollers or wheels are adjustable in respect of height.

10. The optical observation system of claim 1, wherein the support surface is of a flexible and/or vibration-damping configuration.

11. The optical observation system of claim 1, wherein the lifting device is operable for lifting the support surface not more than about 20 mm from the ground.

12. The optical observation system of claim 1, wherein the extendable wheels or rollers are of such a nature, that when the support stand base is raised, the wheels or rollers rest loosely on the ground and, in the event of an abrupt failure of the compressed air, carry the support stand.

13. The optical observation system of claim 1, wherein the extendable wheels or rollers have a springing arrangement.

14. The displaceable support stand of claim 1, wherein the wheels or extendable rollers serve as a displacement device which permits displacement of the support stand, and which comprises a roller lifting device for lifting the support surface above the ground.

15. The optical observation system of claim 1, wherein a lever mechanism is present for effecting the extension of the extendable rollers mechanically.

16. The optical observation system of claim 1, wherein the extension of the extendable rollers is effected electrically.

17. An optical observation system of comprising:
a microscope;
a displaceable microscope support stand carrying the microscope, the displaceable support stand comprising a support stand base which includes a support surface adapted for resting on the ground; and
a compressed air-operated lifting device for lifting the support surface above the ground, a displacement device which permits displacement of the support stand, wheels or rollers which are extendable to project beyond the support surface, and at least one support stand axis with which there is associated a compressed air-operated drive and/or a compressed air-operated brake.

18. The optical observation system of claim 17, wherein the lifting device is operable for lifting the support surface not more than about 20 mm from the ground.

19. An optical observation system comprising:
a microscope and
a displaceable microscope support stand carrying the microscope, the displaceable microscope support stand comprising a support stand base which includes an underside which is adapted for resting flat on the ground as a support surface, and at least one compressed air nozzle which is connected to a compressed air supply and arranged such as for producing an air cushion under the support surface, the compressed air nozzle forming a lifting device for lifting the support surface above the ground and a displacement device which permits displacement of the support stand by means of the air cushion, wherein the support stand is provided with wheels or rollers which are extendable such as to project beyond the support surface.

* * * * *